United States Patent
Yang et al.

(10) Patent No.: US 12,017,182 B2
(45) Date of Patent: Jun. 25, 2024

(54) METHOD AND SYSTEM FOR REFINING LONG CHAIN DICARBOXYLIC ACID

(71) Applicants: Cathay Biotech Inc., Shanghai (CN); CIBT America Inc., Newark, DE (US); Cathay (Jinxiang) Biomaterial Co., Ltd., Shandong (CN)

(72) Inventors: Chen Yang, Shanghai (CN); Bingbing Qin, Shanghai (CN); Yufeng Yang, Shanghai (CN); Kai Wang, Shanghai (CN); Xiucai Liu, Shanghai (CN)

(73) Assignees: Cathay Biotech Inc., Shanghai (CN); CIBT America Inc., Newark, DE (US); Cathay (Jinxiang) Biomaterial Co., Ltd., Shandong (CN)

( * ) Notice: Subject to any disclaimer, the term of this patent is extended or adjusted under 35 U.S.C. 154(b) by 345 days.

(21) Appl. No.: 17/507,959

(22) Filed: Oct. 22, 2021

(65) Prior Publication Data
US 2022/0080357 A1 Mar. 17, 2022

Related U.S. Application Data (63) Continuation-in-part of application No. 16/887,215, filed on May 29, 2020, now Pat. No. 11,155,512.

(30) Foreign Application Priority Data

Dec. 24, 2019 (CN) .......................... 201911347657.4

(51) Int. Cl.
  *B01D 15/08* (2006.01)
  *B01D 3/10* (2006.01)
  (Continued)

(52) U.S. Cl.
  CPC .............. *B01D 61/18* (2013.01); *B01D 3/10* (2013.01); *B01D 3/12* (2013.01); *B01D 9/005* (2013.01);
  (Continued)

(58) Field of Classification Search
  CPC . B01D 3/10; B01D 3/12; B01D 25/12; B01D 29/00; B01D 36/00; B01D 61/18
  See application file for complete search history.

(56) References Cited

U.S. PATENT DOCUMENTS 6,288,275 B1 9/2001 Turner
9,272,976 B2 3/2016 Schulze et al.
(Continued)

FOREIGN PATENT DOCUMENTS

CN        1351006 A    5/2002
CN        1570124 A    1/2005
(Continued)

OTHER PUBLICATIONS

Hao B—CN-108101775-A machine translation—Jun. 1, 2018 (Year: 2018).*

(Continued)

*Primary Examiner* — Bradley R Spies
(74) *Attorney, Agent, or Firm* — Fox Rothschild LLP (57) ABSTRACT

The present disclosure provides a system for refining long chain dicarboxylic acid, comprising: a first membrane filtration unit, for a first membrane filtration of a long chain dicarboxylic acid fermentation broth or a treated liquid therefrom; a first decolorization unit, for carrying out a first decolorization treatment to the filtrate obtained after the membrane filtration; a first acidification/crystallization unit, for carrying out a first acidification/crystallization of a filtrate obtained after the membrane filtration to give a solid-liquid mixture; a first separation unit, for a solid-liquid separation of the solid-liquid mixture; a drying unit, for drying the solid separated by the separation unit to give a first solid. By using the refining system according to the present disclosure, the purity of the obtained product is high, and the disadvantages such as poor quality of the product (Continued)

obtained by crystallization from a solvent and environment pollution caused by a solvent can be overcome.

31 Claims, 1 Drawing Sheet

(51) Int. Cl.
| | |
|---|---|
| *B01D 3/12* | (2006.01) |
| *B01D 9/00* | (2006.01) |
| *B01D 25/12* | (2006.01) |
| *B01D 29/00* | (2006.01) |
| *B01D 36/00* | (2006.01) |
| *B01D 61/14* | (2006.01) |
| *B01D 61/18* | (2006.01) |
| *B01D 61/36* | (2006.01) |
| *B01D 69/02* | (2006.01) |

(52) U.S. Cl.
CPC ........... *B01D 9/0068* (2013.01); *B01D 15/08* (2013.01); *B01D 25/12* (2013.01); *B01D 29/00* (2013.01); *B01D 36/00* (2013.01); *B01D 61/145* (2013.01); *B01D 61/147* (2013.01); *B01D 61/149* (2022.08); *B01D 61/364* (2013.01); *B01D 69/02* (2013.01); B01D 2009/0086 (2013.01); B01D 2311/103 (2013.01); B01D 2311/106 (2013.01); B01D 2311/2626 (2013.01); B01D 2311/2642 (2013.01); B01D 2311/2649 (2013.01); B01D 2311/2669 (2013.01); B01D 2317/025 (2013.01); B01D 2325/0283 (2022.08); B01D 2325/20 (2013.01)

(56) References Cited

U.S. PATENT DOCUMENTS

| | | |
|---|---|---|
| 9,517,996 B2 | 12/2016 | Laplaza et al. |
| 2013/0096343 A1 | 4/2013 | Tietz et al. |
| 2013/0116471 A1* | 5/2013 | Yan .................. C07C 51/42 562/593 |
| 2016/0159723 A1 | 6/2016 | Smith et al. |
| 2017/0217871 A1 | 8/2017 | Schütze et al. |
| 2018/0290961 A1* | 10/2018 | Schütze ............... B01D 61/026 |

FOREIGN PATENT DOCUMENTS

| | | | |
|---|---|---|---|
| CN | 1292072 C | * | 12/2006 |
| CN | 1887843 A | | 1/2007 |
| CN | 101108928 A | | 1/2008 |
| CN | 101177650 A | | 5/2008 |
| CN | 102329224 A | | 1/2012 |
| CN | 102476987 A | | 5/2012 |
| CN | 102775292 A | | 11/2012 |
| CN | 102976917 A | | 3/2013 |
| CN | 103012106 A | | 4/2013 |
| CN | 103570525 A | | 2/2014 |
| CN | 102503800 B | | 6/2014 |
| CN | 104862348 A | | 8/2015 |
| CN | 106660924 A | | 5/2017 |
| CN | 108017535 A | | 5/2018 |
| CN | 108101775 A | * | 6/2018 |
| CN | 109516913 A | | 3/2019 |
| CN | 110272341 A | | 9/2019 |
| CN | 211445569 U | | 9/2020 |
| CN | 211445570 U | | 9/2020 |
| DE | 102015216815 A1 | | 3/2017 |
| JP | S50149616 A | | 11/1975 |
| JP | S5615696 A | | 2/1981 |
| JP | S63258830 A | | 10/1988 |
| JP | S64016743 A | | 1/1989 |
| JP | 2000169426 A | | 6/2000 |
| JP | 2000302724 A | | 10/2000 |
| JP | 2005194211 A | | 7/2005 |
| JP | 2012180306 A | | 9/2012 |
| JP | 2013079224 A | | 5/2013 |
| JP | 2013529603 A | | 7/2013 |
| JP | 2021098685 A | | 7/2021 |
| JP | 7209668 B2 | | 1/2023 |

OTHER PUBLICATIONS

Hu B—CN-1292072-C machine translation—Dec. 27, 2006 (Year: 2006).*
Extended European Search Report issued Oct. 11, 2020 in related EP Application No. 20178389.1; 6 pgs.
JPS 5615695 (A), Mitsui Petrochemical IND, Recovery of dicarboxylic acid, English translation, 6 pgs. (Year: 1981).
First Office Action issued on Jan. 17, 2024 in CN Appl. No. 201911347657.4 with English translation.
First Office Action issued on Jan. 16, 2024 in CN Appl. No. 201911320839.2 with English translation.
Extended European Search Report mailed on Nov. 12, 2020 in EP Appl. No. 20178388.3-1104.
First Office Action drafted on May 24, 2021 for Japanese Appl. No. 2020-097793 with English translation.
Second Office Action drafted on Dec. 20, 2021 for Japanese Appl. No. 2020-097793 with English translation.
First Office Action drafted on Sep. 13, 2023 in Japanese Appl. No. 2022-164833 with English translation.
Second Office Action drafted on Feb. 16, 2024 in Japanese Appl. No. 2022-164833 with English translation.
Non-Final Office Action issued on Apr. 15, 2021 in U.S. Appl. No. 16/887,153.

* cited by examiner

METHOD AND SYSTEM FOR REFINING LONG CHAIN DICARBOXYLIC ACID

CROSS REFERENCE

This application is a continuation-in-part of U.S. patent application Ser. No. 16/887,215, filed on May 29, 2020, which is based upon and claims priority to Chinese Patent Application No. 201911347657.4, filed on Dec. 24, 2019, the entire contents thereof are incorporated herein by reference.

TECHNICAL FIELD

The present disclosure relates to long chain dicarboxylic acid, specifically to a method and a system for refining long chain dicarboxylic acid produced by biological fermentation.

BACKGROUND ART

Long chain dicarboxylic acids (LCDAs, abbreviated as DCn, n=9 to 18) are a group of important organic intermediates, which are widely used in fields such as chemical engineering, light industry, agricultural chemicals, medicine and new materials. Currently, the most conventional method for preparing long chain dicarboxylic acid is biological fermentation of long carbon chain alkane, fatty acid, fatty acid ester or fatty acid salt in the presence of a specific strain. The technologies for extracting and purifying long chain dicarboxylic acid also affect the cost of the final industrially produced dicarboxylic acid. Therefore, the development of a simple and highly efficient technology for extracting and purifying dicarboxylic acid will promote the application of the fermentation technology.

Currently, long chain dicarboxylic acid is normally purified by recrystallization with an organic solvent. CN102503800A discloses a method for refining long chain dicarboxylic acid, in which the long chain dicarboxylic acid crude product is recrystallized with an alcohol or acetone as the solvent to give refined long chain dicarboxylic acid. Although the yield of refining may be improved by diluted solvent, refining long chain dicarboxylic acid with an alcohol as the solvent has a disadvantage that the dicarboxylic acid and ethanol undergo esterification at an elevated temperature, producing new products during the refining process, which affects the purity of the product.

In addition, the recrystallization treatment mainly utilizes the difference in the solubility to remove impurities. However, some impurities may have similar solubility with the long chain dicarboxylic acid, which cannot be completely removed even with repeated recrystallization. The product obtained by crystallization from an organic solvent has a problem of residual solvent.

SUMMARY OF INVENTION

The present disclosure provides a system for refining long chain dicarboxylic acid, comprising:
  a first membrane filtration unit, for a membrane filtration of a long chain dicarboxylic acid fermentation broth or a treated liquid therefrom;
  a first decolorization unit, for carrying out a first decolorization treatment to the filtrate obtained after the membrane filtration;
  a first acidification/crystallization unit, for carrying out an acidification/crystallization of a filtrate obtained after the membrane filtration to give a solid-liquid mixture;
  a first separation unit, for a solid-liquid separation of the solid-liquid mixture;
  a drying unit, for drying the solid separated by the separation unit to give a first solid.

By using the refining system according to one embodiment of the present disclosure, the purity of the obtained product is high, and the disadvantages such as high requirements on equipments by crystallization from the solvent, need of a solvent recovery system, test of solvent safety, environment pollution caused by the solvent can be overcome.

SPECIFIC EMBODIMENTS

Typical embodiments reflecting the features and advantages of the present disclosure will be detailed in the description below. It shall be understood that the present disclosure may have various changes in different embodiments, without departing from the scope of the present disclosure, and the description and figures therein are illustrative in nature, not limiting the present disclosure. In the description, the terms "first", "second", etc., are used to distinguish a variety of processes or products with the same names, not limiting thereto.

An embodiment of the present disclosure provides a method for refining long chain dicarboxylic acid from a long chain dicarboxylic acid fermentation broth or a treated liquid therefrom, said method comprising:
  (1) subjecting the long chain dicarboxylic acid fermentation broth or a treated liquid therefrom to a membrane filtration, an acidification/crystallization, a solid-liquid separation and drying to give a long chain dicarboxylic acid crude product;
  (2) subjecting the long chain dicarboxylic acid crude product to a vacuum distillation to give the long chain dicarboxylic acid product;
  wherein the pressure in the vacuum distillation is ≤100 Pa, preferably ≤50 Pa.

In the present disclosure, the long chain dicarboxylic acid fermentation broth may be a fermentation broth obtained by microbial fermentation using alkane, fatty acid or a derivative thereof as the substrate; and the microorganism converts the terminal methyl group of alkane, fatty acid or fatty acid derivative to carboxyl group through oxidation, so as to produce a long chain dicarboxylic acid.

In an embodiment, the treated liquid from the long chain dicarboxylic acid fermentation broth is a liquid obtained after removing one or more components other than the long chain dicarboxylic acid salt from the fermentation broth or reducing the contents thereof. For example, the fermentation broth is subjected to centrifugation or membrane filtration to separate out the bacterial body and the residual substrate to give the treated liquid.

In an embodiment, the long chain dicarboxylic acid is a $C_9$-$C_{18}$ dicarboxylic acid.

In an embodiment, the long chain dicarboxylic acid is a linear saturated or non-saturated dicarboxylic acid; and has carboxyl groups at both ends.

In an embodiment, the long chain dicarboxylic acid may be one or more of azelaic acid, sebacic acid, undecandioic acid, dodecanedioic acid, tridecandioic acid, tetradecandioic acid, pentadecandioic acid, hexadecandioic acid, heptadecandioic acid, octadecandioic acid and 9-octadecene diacid.

In an embodiment, before the membrane filtration, a base may be added to the fermentation broth or the treated liquid therefrom to dissolve the long chain dicarboxylic acid.

In an embodiment, the pH of the fermentation broth or the treated liquid therefrom may be adjusted to 6 to 12, preferably 8 to 11, such as 8.2, 8.5, 8.8, 9.0, 9.2, 9.5, 9.8, 10.0, 10.2, 10.5, 10.8 or 11.5. The base added may be sodium hydroxide or potassium hydroxide.

In an embodiment, before the membrane filtration, the fermentation broth or the treated liquid therefrom may be heated to 60 to 100° C., such as 62° C., 65° C., 68° C., 70° C., 72° C., 75° C., 78° C., 80° C., 82° C., 85° C., 88° C., 90° C., 92° C., 95° C. or 98° C.

In an embodiment, the membrane filtration includes an ultrafiltration membrane filtration and/or a microfiltration membrane filtration.

In an embodiment, the temperature for the microfiltration membrane filtration is 30 to 100° C., preferably 50 to 100° C., more preferably 60 to 100° C., such as 35° C., 40° C., 45° C., 50° C., 55° C., 60° C., 62° C., 65° C., 68° C., 70° C., 72° C., 75° C., 78° C., 80° C., 82° C., 84° C., 85° C., 86° C., 88° C., 90° C., 92° C., 94° C., 95° C., 96° C. or 98° C.

In an embodiment, the pore size of the microfiltration membrane may be 0.01 to 1 μm, preferably 0.01 to 0.2 μm, more preferably 0.02 to 0.1 μm, such as 0.03 μm, 0.05 μm, 0.08 μm, 0.1 μm, 0.15 μm or 0.5 μm.

In an embodiment, the temperature for the ultrafiltration membrane filtration is 20 to 100° C., preferably 20 to 45° C., more preferably 30 to 40° C., such as 25° C., 30° C., 32° C., 34° C., 35° C., 36° C. or 38° C.

In an embodiment, the cut-off molecular weight of the ultrafiltration membrane may be 1000 to 200000 Da, preferably 1000 to 30000 Da, more preferably 1000 to 10000 Da, such as 1500 Da, 2000 Da, 3000 Da, 4000 Da, 5000 Da, 6000 Da, 8000 Da, 10000 Da, 15000 Da, 20000 Da or 25000 Da.

In an embodiment, the ultrafiltration membrane may be polypropylene membrane, a polysulfone membrane, a polyethersulfone membrane, or an inorganic ultrafiltration membrane, such as a ceramic membrane.

In an embodiment, the membrane filtration includes a microfiltration membrane filtration and an ultrafiltration membrane filtration, in which the fermentation broth or the treated liquid therefrom is first subjected to the microfiltration membrane filtration, and then the filtrate is subjected to the ultrafiltration membrane filtration.

In an embodiment, the fermentation broth or the treated liquid therefrom is subjected to the microfiltration membrane filtration at 60 to 100° C., and the resulted filtrate is cooled to 20 to 45° C., and then subjected to the ultrafiltration membrane filtration.

In step (1) of an embodiment, the filtrate after the membrane filtration is subjected to a decolorization treatment and then to an acidification/crystallization.

In step (1) of an embodiment, the temperature for the decolorization treatment may be 50 to 100° C., preferably 60 to 100° C., more preferably 60 to 80° C., such as 62° C., 65° C., 68° C., 70° C., 72° C., 75° C., 78° C., 80° C., 85° C., 88° C., 90° C. or 95° C.

In step (1) of an embodiment, the duration for the decolorization treatment may be 10 to 180 min, preferably 15 to 120 min, such as 20 min, 30 min, 40 min, 60 min, 70 min, 80 min, 90 min, 100 min, 110 min, 130 min, 150 min or 170 min.

In step (1) of an embodiment, the decolorant used for the decolorization treatment may be activated carbon fiber, activated carbon particle or activated carbon powder, and the amount of the decolorant used may be 0.05 to 5 wt %, such as 1 wt %, 1.5 wt %, 2 wt %, 2.5 wt %, 3 wt %, 3.5 wt % or 4 wt %, relative to the mass of the liquid to be decolorized.

In an embodiment, the acidification/crystallization comprises adjusting the pH of the filtrate to 2 to 5.5 for the crystallization to occur.

In an embodiment, the acidification/crystallization process comprises adjusting the pH of the filtrate obtained by the membrane filtration or the clear liquid obtained by the decolorization treatment to 2 to 4.5, preferably 2 to 4, more preferably 2.5 to 4, more preferably 2.5 to 3.7, such as 2.2, 2.5, 2.8, 3.0, 3.2, 3.5, 3.7, 3.8, 4.0, 4.2, 4.3 or 4.5, to allow the long chain dicarboxylic acid to crystallize and precipitate.

In an embodiment, the pH of the filtrate obtained by the membrane filtration or the clear liquid obtained by the decolorization treatment may be adjusted by adding an acid thereto, which may be an inorganic acid and/or an organic acid. The inorganic acid added may be hydrochloric acid and/or sulfuric acid.

In an embodiment, step (1) comprises:
heating the long chain dicarboxylic acid fermentation broth or the treated liquid therefrom to 30 to 100° C., adjusting its pH to 8 to 11, then subjecting it to a membrane filtration at 20 to 100° C., to give a filtrate;
subjecting the filtrate to a decolorization treatment at 50 to 100° C. to give a clear liquid; and
adjusting the pH of the clear liquid to 2 to 4.5 to allow crystals to precipitate, which are filtered and dried to give the long chain dicarboxylic acid crude product.

In an embodiment, step (2) comprises: subjecting the long chain dicarboxylic acid crude product to a vacuum distillation, and collecting the fraction to give the long chain dicarboxylic acid product.

In an embodiment, the pressure for the vacuum distillation may be 1 to 100 Pa, preferably 1 to 50 Pa, such as 3 Pa, 5 Pa, 6 Pa, 10 Pa, 15 Pa, 20 Pa, 25 Pa, 30 Pa, 50 Pa, 60 Pa or 80 Pa.

In an embodiment, the vacuum distillation includes a molecular distillation and a high vacuum distillation.

In an embodiment, the pressure in the main evaporator for the molecular distillation may be 0.1 to 30 Pa, preferably 0.1 to 15 Pa, such as 1 Pa, 2 Pa, 5 Pa, 6 Pa, 8 Pa, 10 Pa, 12 Pa, 16 Pa, 18 Pa, 20 Pa or 25 Pa.

In an embodiment, the temperature of the evaporation surface of the main evaporator for the molecular distillation is 130 to 250° C., preferably 160 to 230° C., such as 140° C., 150° C., 160° C., 180° C., 200° C., 210° C., 220° C. or 240° C.

In an embodiment, the temperature of the condensation surface of the main evaporator for the molecular distillation is 130 to 160° C., preferably 130 to 150° C., such as 135° C., 140° C., 145° C., 150° C. or 155° C.

In an embodiment, the inlet temperature for the molecular distillation is 130 to 160° C., preferably 135 to 150° C., such as 130° C., 135° C., 140° C., 145° C., 150° C. or 155° C.

In an embodiment, the number of theoretical plates of the rectifying column used in the high vacuum distillation may be 8 to 24, preferably 12 to 20, such as 10, 12, 18 or 24.

Preferably, a packed column is used, and the packing may be that commonly used in the art, such as corrugated wire mesh packing.

In an embodiment, the overhead pressure of the rectifying column used in the high vacuum distillation may be 1 to 100 Pa, preferably 1 to 50 Pa, such as 20 Pa, 30 Pa, 60 Pa, 70 Pa or 80 Pa.

In an embodiment, the overhead temperature of the rectifying column used in the high vacuum distillation may be 160 to 250° C., preferably 180 to 240° C., such as 170° C., 185° C., 190° C., 195° C., 200° C., 210° C., 220° C., 225° C., 228° C., 230° C., 232° C., 235° C., 238° C., 240° C. or 245° C.

In an embodiment, the bottom temperature of the rectifying column used in the high vacuum distillation may be 180 to 270° C., such as 190° C., 200° C., 210° C., 220° C., 230° C., 240° C., 243° C., 245° C., 248° C., 250° C., 255° C., 260° C. or 265° C.

In an embodiment, the reflux ratio in the high vacuum distillation may be (1 to 10):1, preferably (6 to 10):1, such as 1:1, 2:1, 5:1, 6:1, 8:1 or 10:1.

In step (2) of an embodiment, the decolorization treatment may be carried out to the long chain dicarboxylic acid crude product before the vacuum distillation, or to the product obtained after the vacuum distillation.

In step (2) of an embodiment, the decolorization treatment may be a solution decolorization or a melt decolorization.

In an embodiment, the decolorant used for the decolorization treatment may be activated carbon.

In an embodiment, the melt decolorization refers to directly contacting the long chain dicarboxylic acid crude product or the fraction to be decolorized obtained by the vacuum distillation with the decolorant for carrying out the decolorization. For example, the long chain dicarboxylic acid crude product or the fraction obtained by the vacuum distillation is heated and melted, and passed over the decolorant in the melt form.

Both subjecting the long chain dicarboxylic acid crude product to the melt decolorization and then to the vacuum distillation and subjecting the fraction obtained by the vacuum distillation to the melt decolorization can reduce the energy consumption for heating and simplify the process.

In an embodiment, the temperature for the melt decolorization may be 130 to 180° C., preferably 130 to 150° C., such as 135° C., 140° C., 145° C., 150° C., 155° C., 160° C., 165° C., 170° C. or 175° C.

In an embodiment, the amount of the activated carbon used for the melt decolorization is 3 to 50 wt %, preferably 5 to 25 wt %, such as 5 wt %, 10 wt %, 15 wt %, 20 wt %, 25 wt %, 30 wt %, 35 wt %, 40 wt % or 45 wt % of the mass of the long chain dicarboxylic acid crude product or of the mass of the fraction obtained by vacuum distillation.

In an embodiment, after the melt decolorization is completed, the residual activated carbon may be removed by filtration. By the melt decolorization, the substance to be decolorized is decolorized and purified, while introduction of further impurities is avoided.

In an embodiment, the activated carbon used for the decolorization treatment may be one or more of powdered activated carbon, activated carbon fiber, activated carbon particle, activated carbon column.

According to the requirements on the product quality by the customer or by the market, the product obtained by the refining method according to the present disclosure may be further refined to further improve the product quality.

By using the refining method according to an embodiment of the present disclosure, the procedure is simplified, and the disadvantages such as poor quality of the product obtained by crystallization from a solvent and environment pollution caused by a solvent can be overcome.

The refining method according to an embodiment the present disclosure is suitable for purifying long chain dicarboxylic acid produced by biological fermentation. By using the combination of membrane filtration and distillation, especially the combination of a ceramic membrane filtration, an ultrafiltration membrane filtration and a molecular distillation or a high vacuum distillation, no organic solvent is necessary, and the resulted product has a high purity, white color, low ash content, low metal content and low nitrogen content.

An embodiment of the present disclosure provides a long chain dicarboxylic acid obtained by the above refining method.

Figure 1:
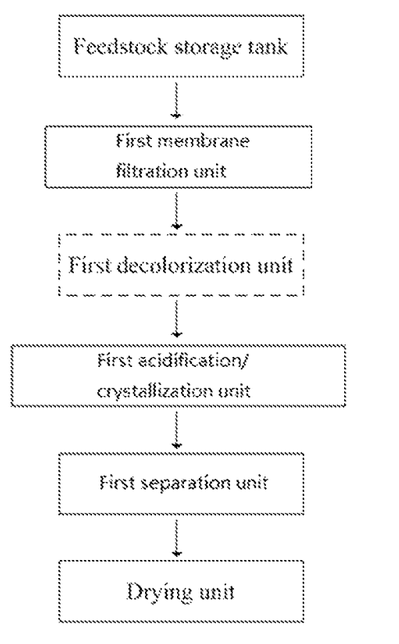
FIG. 1 shows a scheme of the system for refining long chain dicarboxylic acid according to one embodiment of the present disclosure.

As shown in FIG. 1, an embodiment of the present disclosure provides a system for refining long chain dicarboxylic acid which realizes the above refining method, comprises a membrane filtration unit, an acidification/crystallization unit, a separation unit, a drying unit and a vacuum distillation unit, which are sequentially configured.

In an embodiment, the refining system comprises a feedstock storage tank, which may be connected to the membrane filtration unit, for holding the long chain dicarboxylic acid fermentation broth or the treated liquid therefrom.

In an embodiment, the membrane filtration unit is used for the membrane filtration of the long chain dicarboxylic acid fermentation broth or the treated liquid therefrom. A filtration membrane, such as a microfiltration membrane and/or an ultrafiltration membrane, may be disposed in the membrane filtration unit.

In an embodiment, the pore size of the microfiltration membrane may be 0.01 to 1 µm, preferably 0.02 to 0.2 µm, more preferably 0.02 to 0.1 µm, such as 0.03 µm, 0.05 µm, 0.08 µm, 0.1 µm, 0.15 µm or 0.5 µm.

In an embodiment, the cut-off molecular weight of the ultrafiltration membrane may be 1000 to 200000 Da, preferably 1000 to 30000 Da, more preferably 1000 to 10000 Da, such as 1500 Da, 2000 Da, 3000 Da, 4000 Da, 5000 Da, 6000 Da, 8000 Da, 10000 Da, 15000 Da, 20000 Da or 25000 Da.

In an embodiment, the ultrafiltration membrane may be polypropylene membrane, polysulfone membrane, polyethersulfone membrane, or an inorganic ultrafiltration membrane, such as a ceramic membrane.

In an embodiment, the refining system comprises a heating device for heating the feedstock storage tank, so that the long chain dicarboxylic acid fermentation broth or the treated liquid therefrom is subjected to the membrane filtration at a certain temperature, such as 50 to 100° C.

In an embodiment, the long chain dicarboxylic acid fermentation broth is subjected to a membrane filtration in the membrane filtration unit to give a filtrate. An acidification/crystallization unit is used for an acidification/crystallization of the filtrate.

In an embodiment, the acidification/crystallization unit comprises an acidification tank, in which the filtrate undergoes the acidification/crystallization to give a solid-liquid mixture.

In an embodiment, a first decolorization unit may be disposed between the membrane filtration unit and the acidification/crystallization unit, so that the filtrate is subjected to the decolorization treatment and then to the acidification/crystallization.

In an embodiment, the first decolorization unit may comprise a decolorization tank and a filter. The decolorization tank is used for mixing the liquid to be decolorized and the solid decolorant for carrying out the decolorization. After the decolorization is completed, the solid decolorant may be filtered out by the filter which may be a plate-and-frame filter.

In an embodiment, the first decolorization unit comprises a heating device for heating the decolorization tank, so that the decolorization treatment is carried out at a certain temperature (e.g., 50 to 100° C.).

In an embodiment, the separation unit is used for a solid-liquid separation of the solid-liquid mixture obtained in the acidification/crystallization unit.

In an embodiment, the separation unit may comprise a filtration device or a centrifuge.

In an embodiment, the drying unit comprises a heating device for heating and drying the solid obtained by the separation unit to give the long chain dicarboxylic acid crude product.

In an embodiment, a vacuum distillation unit is used to distill and separate the dried long chain dicarboxylic acid crude product to give the long chain dicarboxylic acid product.

In an embodiment, the vacuum distillation unit comprises a heating device to bring the long chain dicarboxylic acid crude product to the melting state.

In an embodiment, the vacuum distillation unit comprises a distillation device for carrying out the vacuum distillation process.

In an embodiment, the distillation device comprises a molecular distillation device for carrying out a molecular distillation.

In another embodiment, the distillation device comprises a rectifying column for carrying out a high vacuum distillation.

In an embodiment, the number of theoretical plates in the rectifying column may be 8 to 24, preferably 12 to 20, such as 10, 12, 18 or 24.

In an embodiment, the refining system comprises a second decolorization unit.

In an embodiment, the second decolorization unit may comprise a decolorization tank and a filter. The decolorization tank is used for mixing the liquid to be decolorized and the solid decolorant for carrying out the decolorization. After the decolorization is completed, the solid decolorant may be filtered out by the filter which may be a plate-and-frame filter.

In an embodiment, the long chain dicarboxylic acid crude product or the fraction obtained by the vacuum distillation is directly contacted with the decolorant in the second decolorization unit for carrying out a decolorization. For example, the long chain dicarboxylic acid crude product or the fraction obtained by the vacuum distillation flows over the decolorant in the second decolorization unit in a melting state.

In an embodiment, the second decolorization unit comprises a heating device for heating the decolorization tank, so that the decolorization treatment is carried out at a certain temperature (e.g., 130 to 180° C.).

In an embodiment, the second decolorization unit is disposed between the drying unit and the vacuum distillation unit, so that a decolorization treatment of the long chain dicarboxylic acid crude product is carried out before the vacuum distillation. Alternatively, the second decolorization unit is disposed after the vacuum distillation unit, so that the product after the vacuum distillation is subjected to a decolorization treatment.

In another embodiment, the long chain dicarboxylic acid crude product or the fraction obtained by the vacuum distillation is heated and melted, and then decolorized with the decolorant. After the decolorization, the residual decolorant may be removed by filtration to give the second long chain dicarboxylic acid crude product or the long chain dicarboxylic acid product.

In the present disclosure, the acidification tank, the decolorization tank, the dissolution tank and the heating device may be known equipments.

An embodiment of the present disclosure provides a system for refining long chain dicarboxylic acid, comprising
    a first membrane filtration unit, for a first membrane filtration of a long chain dicarboxylic acid fermentation broth or a treated liquid therefrom;
    a first decolorization unit, for carrying out a first decolorization treatment to the filtrate obtained after the membrane filtration
    a first acidification/crystallization unit, for carrying out an acidification/crystallization of a filtrate obtained after the membrane filtration to give a solid-liquid mixture;
    a first separation unit, for a solid-liquid separation of the solid-liquid mixture;
    a drying unit, for drying the solid separated by the separation unit to give a first solid.

In another embodiment, the first membrane filtration unit comprises a microfiltration membrane and/or an ultrafiltration membrane.

In another embodiment, a temperature for the microfiltration membrane filtration is 30 to 100° C.; and/or
    a pore size of the microfiltration membrane is 0.01 to 1 μm; and/or
    the pressure difference on both sides of the membrane during microfiltration filtration is controlled to be 0.05 to 0.5 MPa; and/or
    a temperature for the ultrafiltration membrane filtration is 20 to 100° C.
    a cut-off molecular weight of the ultrafiltration membrane is 1000 to 200000 Da.

In another embodiment, a temperature for the first decolorization treatment is 50 to 100° C.; and/or
    the acidification/crystallization comprises adjusting the filtrate to pH 2 to 4.5 for crystallization to occur.

In another embodiment, the system for refining long chain dicarboxylic acid further comprises a vacuum distillation unit, for carrying out separation by distillation on the first solid to obtain the second solid.

In another embodiment, a pressure of the vacuum distillation is ≤100 Pa; and/or the vacuum distillation unit comprises a molecular distillation device for carrying out a molecular distillation or a rectifying column for carrying out a high vacuum distillation.

In another embodiment, the number of plates of the rectifying column is 8 to 24, and/or,
    the rectifying column has an overhead pressure of 1 to 100 Pa, and/or,
    the rectifying column has an overhead temperature of 160 to 250° C., and/or,
    the rectifying column has a bottom temperature of 180 to 270° C., and/or,
    the rectifying column has a reflux ratio of (1 to 10):1.

In another embodiment, the pressure in the main evaporator for the molecular distillation is 0.1 to 30 Pa, and/or
    the temperature of the evaporation surface of the main evaporator is 130 to 250° C., and/or
    the temperature of the condensation surface of the main evaporator is 130 to 160° C.

In another embodiment, the system for refining long chain dicarboxylic acid comprises a second decolorization unit, which is disposed between the drying unit and the vacuum distillation unit, for carrying out a decolorization treatment to the first solid; or
  the second decolorization unit is disposed after the vacuum distillation unit, for carrying out a decolorization treatment to the product obtained after the vacuum distillation.

In another embodiment, the decolorization treatment comprises a melt decolorization; said melt decolorization comprises heating the solid to be decolorized to melt, and passing the same in melt form over a decolorant.

In another embodiment, the temperature for the melt decolorization is 130 to 180° C.; and/or the decolorant is an activated carbon, in the melt decolorization, the amount of the activated carbon is 3 to 50 wt % of the mass of the solid to be decolorized.

In another embodiment, a second acidification/crystallization unit and a second separation unit are disposed between the second decolorization unit and the vacuum distillation unit.

In another embodiment, the pH of the fermentation broth or the treated liquid therefrom is 6 to 12, preferably 8 to 11; and/or
  before the first membrane filtration, the fermentation broth or the treated liquid therefrom is heated to 60 to 100° C., and/or
  before the first filtration unit, a feedstock storage tank and a heating device are disposed, for heating the fermentation broth or the treated liquid therefrom to 60 to 100° C.

In another embodiment, a microfiltration membrane filtration device, an ultrafiltration membrane filtration device and a cooling device are disposed in the first membrane filtration unit; after the microfiltration membrane filtration, the resulted filtrate from the fermentation broth or the treated liquid therefrom is cooled to 20 to 45° C. in the cooling device, and subjected to the ultrafiltration membrane filtration.

In another embodiment, a second membrane filtration unit, a second decolorization unit, a second acidification/crystallization unit, a second separation unit which are sequentially connected, are disposed between the first separation unit and said drying unit; in the second membrane filtration unit, a dissolution tank and a filtration membrane are disposed, said filtration membrane is an ultrafiltration membrane or a microfiltration membrane.

In another embodiment, a third membrane filtration unit is disposed between the second membrane filtration unit and the second decolorization unit; and/or
  a third membrane filtration unit is disposed between said second decolorization unit and said acidification/crystallization unit.

In another embodiment, a filtration membrane is disposed in the third membrane filtration unit, said membrane filtration unit is an ultrafiltration membrane.

In another embodiment, a decolorization tank, a plate-and-frame filter and a heating device are disposed in the first decolorization unit.

All membrane filtration units, all decolorization units, all acidification/crystallization units, and all separation units mentioned in the present invention may be optionally used multiple times, and each independently has the corresponding various configurations and forms mentioned in the text, of which associated description will not be repeated hereinafter.

In the following, the method for refining long chain dicarboxylic acid according to an embodiment of the present disclosure is described in detail by way of specific examples, in which the raw materials used, without otherwise specified, are all commercially available, and the test methods are as follows:

1. Gas Chromatographic Test of Long Chain Dicarboxylic Acid

A standard long chain dicarboxylic acid sample was used as the control, and GB5413.27-2010 "Determination of fatty acids in foods for infants and young children, milk and milk products" is referred to.

2. Ash Content Test

A test sample was calcined in a crucible, then in a muffle furnace at 700 to 800° C. for 2 hours. After cooling to constant weight, the weight was measured, and the weight percentage was calculated.

3. Total Nitrogen Test

Kjeldahl determination was used.

4. Light Transmittance Test

Substances with different colors have different light transmittances at a certain wavelength. Based on this, the color of the dicarboxylic acid product is represented by the light transmittances of a 25 wt. % solution of the long chain dicarboxylic acid sample in dimethyl sulfoxide at 440 nm.

5. Fe Content Test

Fe content was determined by spectroscopy referring to GB/T3049-2006.

Example A

Following the fermentation method disclosed in Example 4 of CN1570124A, a dodecanedioic acid (DC12) fermentation broth was obtained.

The fermentation broth was fed to a feedstock storage tank and heated to 85° C., the pH of the fermentation broth was adjusted to 8.2 by adding thereto a base, and then fed to the first membrane filtration unit, the fermentation broth was filtered at 85° C. with a ceramic microfiltration membrane having a pore size of 0.05 μm to remove the bacterial body to give a filtrate.

The filtrate was passed into the first decolorization unit, and decolorized with 3 wt % activated carbon at 85° C. for 40 min, and filtered with a plate-and-frame filter to give a clear liquid, which was then fed to the first acidification/crystallization unit, wherein the pH of the clear liquid was adjusted to 2.8 with sulfuric acid to carry out an acidification/crystallization to obtain a solid-liquid mixture, which was then sent to the first separation unit for filtration to obtain the solid.

The resulting solid was dissolved in the dissolution tank of the secondary membrane filtration unit, followed by addition of water and sodium hydroxide to to form a solution upon the dissolution of the solid, the solution was filtered at 85° C. with a ceramic microfiltration membrane having a pore size of 0.05 μm, the filtrate was passed into the second decolorization unit, and decolorized with 3 wt % activated carbon at 85° C. for 40 min, and filtered with a plate-and-frame filter to give a clear liquid, which was then fed to the second acidification/crystallization unit, wherein the pH of the clear liquid was adjusted to 2.8 with sulfuric acid to carry out an acidification/crystallization to obtain a solid-liquid mixture, which was then sent to the second separation unit for filtration to obtain the solid.

The resulting solid was dried over the drying unit to give the DC12 crude product.

The DC12 crude product was sent to the vacuum distillation unit and purified by molecular distillation, in which the pressure in the main evaporator of the molecular distillation device was 18 Pa, the temperature of the evaporation surface of the main evaporator was 180° C., the temperature of the condensation surface of the main evaporator was 140° C., and the feedstock inlet temperature was 130° C. The fraction was collected to give the DC12 product.

Example B

Following the fermentation method disclosed in Example 4 of CN1570124A, a dodecanedioic acid (DC12) fermentation broth was obtained.

The fermentation broth was fed to a feedstock storage tank and heated to 85° C., the pH of the fermentation broth was adjusted to 8.2 by adding thereto a base, and then fed to the first membrane filtration unit, the fermentation broth was filtered at 85° C. with a ceramic microfiltration membrane having a pore size of 0.05 μm to remove the bacterial body to give a filtrate.

The filtrate was passed into the first decolorization unit, and decolorized with 3 wt % activated carbon at 85° C. for 40 min, and filtered with a plate-and-frame filter to give a clear liquid, which was then fed to the first acidification/crystallization unit, wherein the pH of the clear liquid was adjusted to 2.8 with sulfuric acid to carry out an acidification/crystallization to obtain a solid-liquid mixture, which was then sent to the first separation unit for filtration to obtain the solid.

The resulting solid was dissolved in the dissolution tank of the secondary membrane filtration unit, followed by addition of water and sodium hydroxide to form a solution upon the dissolution of the solid, the solution was filtered at 30° C. with an ultrafiltration membrane having a cut-off molecular weight of 5000 Da, to give a filtrate, which was then passed into the second decolorization unit, and decolorized with 3 wt % activated carbon at 85° C. for 40 min, and filtered with a plate-and-frame filter to give a clear liquid, which was then fed to the second acidification/crystallization unit, wherein the pH of the clear liquid was adjusted to 2.8 with sulfuric acid to carry out an acidification/crystallization to obtain a solid-liquid mixture, which was then sent to the second separation unit for filtration to obtain the solid.

The resulting solid was dried over the drying unit to give the DC12 crude product.

The DC12 crude product was sent to the vacuum distillation unit and purified by molecular distillation, in which the pressure in the main evaporator of the molecular distillation device was 18 Pa, the temperature of the evaporation surface of the main evaporator was 180° C., the temperature of the condensation surface of the main evaporator was 140° C., and the feedstock inlet temperature was 130° C. The fraction was collected to give the DC12 product.

Example C

Following the fermentation method disclosed in Example 4 of CN1570124A, a dodecanedioic acid (DC12) fermentation broth was obtained.

The fermentation broth was fed to a feedstock storage tank and heated to 85° C., the pH of the fermentation broth was adjusted to 8.2 by adding thereto a base, and then fed to the first membrane filtration unit, the fermentation broth was filtered at 85° C. with a ceramic microfiltration membrane having a pore size of 0.05 μm to remove the bacterial body to give a filtrate.

The filtrate was passed into the first decolorization unit, and decolorized with 3 wt % activated carbon at 85° C. for 40 min, and filtered with a plate-and-frame filter to give a clear liquid, which was then fed to the first acidification/crystallization unit, wherein the pH of the clear liquid was adjusted to 2.8 with sulfuric acid to carry out an acidification/crystallization to obtain a solid-liquid mixture, which was then sent to the first separation unit for filtration to obtain the solid.

The resulting solid was dissolved in the dissolution tank of the secondary membrane filtration unit, followed by addition of water and sodium hydroxide to form a solution upon the dissolution of the solid, the solution was filtered at 90° C. with a ceramic microfiltration membrane having a pore size of 0.05 μm, and then cooled to 30° C. by a cooling device, and filtered at 30° C. with an ultrafiltration membrane having a cut-off molecular weight of 5000 Da, to give a filtrate, which was then passed into the second decolorization unit, and decolorized with 3 wt % activated carbon at 85° C. for 40 min, and filtered with a plate-and-frame filter to give a clear liquid, which was then fed to the second acidification/crystallization unit, wherein the pH of the clear liquid was adjusted to 2.8 with sulfuric acid to carry out an acidification/crystallization to obtain a solid-liquid mixture, which was then sent to the second separation unit for filtration to obtain the solid.

The resulting solid was dried over the drying unit to give the DC12 crude product.

The DC12 crude product was sent to the vacuum distillation unit and purified by a molecular distillation, in which the pressure in the main evaporator of the molecular distillation device was 18 Pa, the temperature of the evaporation surface of the main evaporator was 180° C., the temperature of the condensation surface of the main evaporator was 140° C., and the feedstock inlet temperature was 130° C. The fraction was collected to give the DC12 product.

Example D

Following the fermentation method disclosed in Example 4 of CN1570124A, a dodecanedioic acid (DC12) fermentation broth was obtained.

The fermentation broth was fed to a feedstock storage tank and heated to 85° C., the pH of the fermentation broth was adjusted to 8.2 by adding thereto a base, and then fed to the first membrane filtration unit, the fermentation broth was filtered at 85° C. with a ceramic microfiltration membrane having a pore size of 0.05 μm to remove the bacterial body to give a filtrate.

The filtrate was passed into the first decolorization unit, and decolorized with 3 wt % activated carbon at 85° C. for 40 min, and filtered with a plate-and-frame filter to give a clear liquid, which was then fed to the first acidification/crystallization unit, wherein the pH of the clear liquid was adjusted to 2.8 with sulfuric acid to carry out an acidification/crystallization to obtain a solid-liquid mixture, which was then sent to the first separation unit for filtration to obtain the solid.

The resulting solid was dissolved in the dissolution tank of the secondary membrane filtration unit, followed by addition of water and sodium hydroxide to form a solution upon the dissolution of the solid, and the solution was filtered at 30° C. with an ultrafiltration membrane having a cut-off molecular weight of 10000 Da, to give a filtrate, which was then passed into the second decolorization unit, and decolorized with 3 wt % activated carbon at 85° C. for 40 min, and filtered with a plate-and-frame filter to give a clear liquid, and the clear liquid was filtered at 30° C. with an ultrafiltration membrane having a cut-off molecular weight of 5000 Da, to give a filtrate, which was then fed to the second acidification/crystallization unit, wherein the pH of the clear liquid was adjusted to 2.8 with sulfuric acid to carry out an acidification/crystallization to obtain a solid-liquid mixture, which was then sent to the second separation unit for filtration to obtain the solid.

The resulting solid was dried over the drying unit to give the DC12 crude product.

The DC12 crude product was purified by a high vacuum distillation, in which the rectifying column had a plate number of 12, an overhead pressure of 60 Pa, an overhead temperature of 238° C., a bottom temperature of 250° C., and a reflux ratio of 5:1. The fraction was collected and cooled to give the DC12 product.

Example 1. DC12, Microfiltration Membrane Filtration+Molecular Distillation

Following the fermentation method disclosed in Example 4 of CN1570124A, a dodecanedioic acid (DC12) fermentation broth was obtained.

The fermentation broth was fed to a feedstock storage tank and heated to 85° C., the pH of the fermentation broth was adjusted to 8.2 by adding thereto a base, and then fed to the membrane filtration unit, the fermentation broth was filtered at 85° C. with a ceramic microfiltration membrane having a pore size of 0.05 μm to remove the bacterial body to give a filtrate.

The filtrate was passed into the first decolorization unit, and decolorized with 3 wt % activated carbon at 85° C. for 40 min, and filtered with a plate-and-frame filter to give a clear liquid, which was then fed to the acidification/crystallization unit, wherein the pH of the clear liquid was adjusted with sulfuric acid to pH 2.8 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a molecular distillation, in which the pressure in the main evaporator of the molecular distillation device was 18 Pa, the temperature of the evaporation surface of the main evaporator was 180° C., the temperature of the condensation surface of the main evaporator was 140° C., and the feedstock inlet temperature was 130° C. The fraction was collected to give the DC12 product.

Example 2. DC12, Microfiltration Membrane Filtration+High Vacuum Distillation Following the fermentation method disclosed in Example 4 of CN1570124A, a dodecanedioic acid fermentation broth was obtained.

The fermentation broth was fed to a feedstock storage tank and heated to 85° C., the pH of the fermentation broth was adjusted to 8.2 by adding thereto a base, and then fed to the membrane filtration unit, the fermentation broth was filtered at 85° C. with a ceramic microfiltration membrane having a pore size of 0.05 μm to remove the bacterial body to give a filtrate.

The filtrate was passed into the first decolorization unit, and decolorized with 3 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 2.8 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a high vacuum distillation, in which the rectifying column had a plate number of 12, an overhead pressure of 60 Pa, an overhead temperature of 238° C., a bottom temperature of 250° C., and a reflux ratio of 5:1. The fraction was collected and cooled to give the DC12 product.

Example 3. DC16, Microfiltration Membrane Filtration+Ultrafiltration Membrane Filtration+Molecular Distillation Following the fermentation method disclosed in Example 8 of CN1570124A, a hexadecandioic acid (DC16) fermentation broth was obtained.

The fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 30° C. by a cooling device, and filtered at 30° C. with an ultrafiltration membrane having a cut-off molecular weight of 5000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with hydrochloric acid to pH 3.0 to carry out an acidification/crystallization to obtain a solid-liquid mixture, which was then sent to the separation unit for filtration to obtain the solid, the resulting solid was dried over the drying unit to give the DC16 crude product.

The DC16 crude product was sent to the vacuum distillation unit and purified by a molecular distillation, in which the pressure in the main evaporator of the molecular distillation device was 6 Pa, the temperature of the evaporation surface of the main evaporator was 200° C., the temperature of the condensation surface of the main evaporator was 150° C., and the feedstock inlet temperature was 140° C. The fraction was collected and cooled to give the DC16 product.

Example 4-1. DC12, Microfiltration Membrane Filtration+Ultrafiltration Membrane Filtration+Molecular Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 5000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 3.0 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a molecular distillation, in which the pressure in the main evaporator of the molecular distillation device was 5 Pa, the temperature of the evaporation surface of the main evaporator was 180° C., the temperature of the condensation surface of the main evaporator was 140° C., and the feedstock inlet temperature was 130° C. The fraction was collected and cooled to give the DC12 product.

Example 4-2. DC12, Microfiltration Membrane Filtration+Ultrafiltration Membrane Filtration+Molecular Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.15 μm to remove the bacterial body, then cooled to 35° C. by a cooling device, and filtered at 35° C. with an ultrafiltration membrane having a cut-off molecular weight of 15000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 4 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a molecular distillation, in which the pressure in the main evaporator of the molecular distillation device was 8 Pa, the temperature of the evaporation surface of the main evaporator was 180° C., the temperature of the condensation surface of the main evaporator was 140° C., and the feedstock inlet temperature was 130° C. The fraction was collected and cooled to give the DC12 product.

Example 4-3. DC12, Microfiltration Membrane Filtration+Ultrafiltration Membrane Filtration+Molecular Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 15000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 4.5 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a molecular distillation, in which the pressure in the main evaporator of the molecular distillation device was 18 Pa, the temperature of the evaporation surface of the main evaporator was 150° C., the temperature of the condensation surface of the main evaporator was 130° C., and the feedstock inlet temperature was 130° C. The fraction was collected and cooled to give the DC12 product.

Example 5-1. DC12, Microfiltration Membrane Filtration+Ultrafiltration Membrane Filtration+High Vacuum Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 5000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 3.0 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a high vacuum distillation, in which the rectifying column had a plate number of 10, an overhead pressure of 30 Pa, an overhead temperature of 230° C., a bottom temperature of 243° C., and a reflux ratio of 5:1. The fraction was collected and cooled to give the DC12 product.

Example 5-2. DC12, Microfiltration Membrane Filtration+Ultrafiltration Membrane Filtration+High Vacuum Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.15 μm to remove the bacterial body, then cooled to 35° C. by a cooling device, and filtered at 35° C. with an ultrafiltration membrane having a cut-off molecular weight of 12000 Da, to give a filtrate.

The filtrate was passed into the first decolorization unit, and decolorized with 2 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 4.2 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a high vacuum distillation, in which the rectifying column had a plate number of 24, an overhead pressure of 30 Pa, an overhead temperature of 240° C., a bottom temperature of 252° C., and a reflux ratio of 5:1. The fraction was collected and cooled to give the DC12 product.

Example 5-3. DC12, Microfiltration Membrane Filtration+Ultrafiltration Membrane Filtration+High Vacuum Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 5000 Da, to give a filtrate.

The filtrate was passed into the first decolorization unit, and decolorized with 2 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 3 to carry out an acidification/crystallization to obtain a solid-liquid mixture, which was then sent to the separation unit for filtration to obtain the solid, the resulting solid was dried over the drying unit to give the DC12 crude product.

The DC12 crude product was sent to the vacuum distillation unit and purified by a high vacuum distillation, in which the rectifying column had a plate number of 24, an overhead pressure of 30 Pa, an overhead temperature of 240° C., a bottom temperature of 252° C., and a reflux ratio of 7:1. The fraction was collected and cooled to give the DC12 product.

Example 6-1. DC12, Microfiltration Membrane Filtration+Ultrafiltration Membrane Filtration+Melt Decolorization of Crude Product+High Vacuum Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.25 μm to remove the bacterial body, then cooled to 35° C. by a cooling device, and filtered at 35° C. with an ultrafiltration membrane having a cut-off molecular weight of 20000 Da, to give a filtrate. The filtrate was passed into the first decolorization unit, and decolorized with 2 wt % activated carbon at 85° C. for 20 min, and filtered with a plate-and-frame filter to give a clear liquid.

The clear liquid was fed to the acidification/crystallization unit, wherein the pH of the clear liquid was adjusted with sulfuric acid to pH 4.5 to carry out an acidification/crystallization to obtain a solid-liquid mixture, which was then sent to the separation unit for filtration to obtain the solid, the resulting solid was dried over the drying unit to give the DC12 crude product.

The DC12 crude product was heated and melted, and then decolorized with an activated carbon column composed of activated carbon particles at 150° C., in which the mass of the activated carbon particles was 40% of the mass of the DC12 crude product.

The decolorized DC12 crude product was sent to the vacuum distillation unit and purified by a high vacuum distillation, in which the rectifying column had a plate number of 20, an overhead pressure of 30 Pa, an overhead temperature of 230° C., a bottom temperature of 245° C., and a reflux ratio of 5:1. The fraction was collected and cooled to give the DC12 product.

Example 6-2. DC12, Microfiltration Membrane Filtration+Ultrafiltration Membrane Filtration+Melt Decolorization of Crude Product+High Vacuum Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.15 μm to remove the bacterial body, then cooled to 35° C. by a cooling device, and filtered at 35° C. with an ultrafiltration membrane having a cut-off molecular weight of 5000 Da, to give a filtrate. The filtrate was passed into the first decolorization unit, and decolorized with 2 wt % activated carbon at 85° C. for 20 min, and filtered with a plate-and-frame filter to give a clear liquid.

The clear liquid was fed to the acidification/crystallization unit, wherein the pH of the clear liquid was adjusted with sulfuric acid to pH 3 to carry out an acidification/crystallization to obtain a solid-liquid mixture, which was then sent to the separation unit for filtration to obtain the solid, the resulting solid was dried over the drying unit to give the DC12 crude product.

The DC12 crude product was heated and melted, and then decolorized with an activated carbon column composed of activated carbon particles at 150° C., in which the mass of the activated carbon particles was 40% of the mass of the DC12 crude product.

The decolorized DC12 crude product was sent to the vacuum distillation unit and purified by a high vacuum distillation, in which the rectifying column had a plate number of 22, an overhead pressure of 30 Pa, an overhead temperature of 230° C., a bottom temperature of 252° C., and a reflux ratio of 8:1. The fraction was collected and cooled to give the DC12 product.

Example 6-3. DC12, Microfiltration Membrane Filtration+Ultrafiltration Membrane Filtration+Melt Decolorization of Crude Product+High Vacuum Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 5000 Da, to give a filtrate. The filtrate was passed into the first decolorization unit, and decolorized with 2 wt % activated carbon at 85° C. for 20 min, and filtered with a plate-and-frame filter to give a clear liquid.

The clear liquid was fed to the acidification/crystallization unit, wherein the pH of the clear liquid was adjusted with sulfuric acid to pH 3 to carry out an acidification/crystallization to obtain a solid-liquid mixture, which was then sent to the separation unit for filtration to obtain the solid, the resulting solid was dried over the drying unit to give the DC12 crude product.

The DC12 crude product was heated and melted, and then decolorized with an activated carbon column composed of activated carbon particles at 140° C., in which the mass of the activated carbon particles was 25% of the mass of the DC12 crude product.

The decolorized DC12 crude product was sent to the vacuum distillation unit and purified by a high vacuum distillation, in which the rectifying column had a plate number of 18, an overhead pressure of 30 Pa, an overhead temperature of 240° C., a bottom temperature of 250° C., and a reflux ratio of 5:1. The fraction was collected and cooled to give the DC12 product.

Example 7. DC12, Microfiltration Membrane Filtration+Ultrafiltration Membrane Filtration+Melt Decolorization of Crude Product+Molecular Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 5000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 3.0 to carry out an acidification/crystallization to obtain a solid-liquid mixture, which was then sent to the separation unit for filtration to obtain the solid, the resulting solid was dried over the drying unit to give the DC12 crude product.

The DC12 crude product was heated and melted, and then decolorized with an activated carbon column composed of activated carbon particles at 135° C., in which the mass of the activated carbon particles was 10% of the mass of the DC12 crude product.

The decolorized DC12 crude product was sent to the vacuum distillation unit and purified by a molecular distillation, in which the pressure in the main evaporator of the molecular distillation device was 3 Pa, the temperature of the evaporation surface of the main evaporator was 220° C., the temperature of the condensation surface of the main evaporator was 145° C., and the feedstock inlet temperature was 135° C. The fraction was collected and cooled to give the DC12 product.

Example 8. DC12, Microfiltration Membrane Filtration+Ultrafiltration Membrane Filtration+Melt Decolorization of Crude Product+Molecular Distillation Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the membrane filtration unit, the fermentation broth was filtered at 90° C. with a ceramic microfiltration membrane having a pore size of 0.05 μm to remove the bacterial body, then cooled to 35° C. by a cooling device, and filtered at 35° C. with an ultrafiltration membrane having a cut-off molecular weight of 15000 Da, to give a filtrate.

The filtrate was passed into the first decolorization unit, and decolorized with 2.5 wt % activated carbon at 85° C. for 20 min, and filtered with a plate-and-frame filter to give a clear liquid, which was then fed to the acidification/crystallization unit, wherein the pH of the clear liquid was adjusted with sulfuric acid to pH 4.2 to carry out an acidification/crystallization to obtain a solid-liquid mixture, which was then sent to the separation unit for filtration to obtain the solid, the resulting solid was dried over the drying unit to give the DC12 crude product.

The DC12 crude product was heated and melted, and then decolorized with an activated carbon column composed of activated carbon particles at 135° C., in which the mass of the activated carbon particles was 5% of the mass of the DC12 crude product.

The decolorized DC12 crude product was sent to the vacuum distillation unit and purified by a molecular distillation, in which the pressure in the main evaporator of the molecular distillation device was 16 Pa, the temperature of the evaporation surface of the main evaporator was 180° C., the temperature of the condensation surface of the main evaporator was 140° C., and the feedstock inlet temperature was 130° C. The fraction was collected and cooled to give the DC12 product.

Example 9. DC12, Microfiltration Membrane Filtration+Ultrafiltration Membrane Filtration+Molecular Distillation+Melt Decolorization of Fraction The present example and Example 4-1 were substantially the same in the starting materials used and the procedure, but were different in the following: the fraction obtained in the molecular distillation of Example 4-1 was further decolorized, in which the fraction obtained in the molecular distillation was heated and melted, and then decolorized with an activated carbon column composed of activated carbon particles at 135° C., in which the mass of the activated carbon particles was 15% of the mass of the DC12 crude product, and then cooled to give the DC12 product.

Comparative Example 1. DC12, Centrifugation+Dissolution by Base+Decolorization+Precipitation by Acid Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the centrifugation device to remove the bacterial body by centrifugation to give a clear liquid, which was then fed to the acidification/crystallization unit, wherein the pH of the clear liquid was adjusted with sulfuric acid to pH 3.0 to carry out an acidification/crystallization, the solution was filtered to give a solid, the resulting solid was dried over the drying unit to give the DC12 crude product.

To 100 g of the DC12 crude product was added 1000 g of water, and the solution was mixed in the dissolution tank. The mixture was heated to 70° C., followed by adding caustic soda to adjust the pH to 10. The mixture was stirred so that dodecanedioic acid was completely dissolved. To the resulted solution was added 10 g of microporous powdered sugar charcoal. The mixture was stirred for 1 h and then fed to the separation unit for filtration while hot to give a filtrate. The filtrate was sent to the decolorization tank and further added therein 10 g of microporous powdered sugar charcoal. The mixture was stirred for 1 h and then filtered while hot to give a filtrate. The filtrate was sent to the acidification/crystallization unit, wherein sulfuric acid with a mass percentage concentration of 98% was added to adjust the pH to less than 3. The mixture was cooled to 25° C. to give a solid-liquid mixture, which was then sent to the separation unit for filtration to give the DC12 product.

Comparative Example 2. DC12, Centrifugation+Decolorization+Recrystallization from Ethyl Acetate Following the fermentation method disclosed in Example 4 of CN1570124A, a dodecanedioic acid fermentation broth was obtained.

The DC12 fermentation broth was fed to a feedstock storage tank and heated to 90° C., the pH of the fermentation broth was adjusted to 8.5 by adding thereto a base, and then fed to the centrifugation device to remove the bacterial body by centrifugation. The filtrate was sent to the decolorization unit, and to the filtrate was added activated carbon in an amount of 2.5% of the mass of the filtrate for decolorization at 90° C. for 25 min. The mixture was filtered with a ceramic membrane at 90° C. to give a clear liquid, which was then fed to the acidification/crystallization unit, wherein the pH of the clear liquid was adjusted to pH 3.0 to carry out an acidification/crystallization to obtain a solid-liquid mixture, which was then sent to the separation unit for filtration to obtain the solid, the resulting solid was dried over the drying unit to give the DC12 crude product.

To 300 g of DC12 crude product was added 900 mL of ethyl acetate, and the solution was mixed in the dissolution tank. The mixture was heated to 80° C. to dissolve the crude product. The mixture was fed to the separation unit for filtration and the filtrate was kept at the same temperature for 60 min, then cooled to 25° C. for crystallization to give a solid-liquid mixture, which was then fed to the separation unit for filtration to give the crystallization product. To the product obtained by the crystallization was added 1000 mL of ethyl acetate, which was mixed in a dissolution tank. The mixture was heated to 80° C. to dissolve DC12. The mixture was kept at the same temperature for 30 min, then cooled to 25° C. in 1 h for crystallization to give a solid-liquid mixture. The solid-liquid mixture was fed to the separation unit for filtration, the resulting solid was dried over the drying unit to give the DC12 product.

Comparative Example 3. DC16, Centrifugation+Dissolution by Base+Decolorization+Precipitation by Acid Following the fermentation method disclosed in Example 8 of CN1570124A, a hexadecandioic acid fermentation broth was obtained.

The fermentation broth was fed to a feedstock storage tank and heated to 90° C., the pH of the fermentation broth was adjusted to 8.5 by adding thereto a base, and then fed to the centrifugation device to remove the bacterial body by centrifugation to give a clear liquid, which was then fed to the acidification/crystallization unit, wherein the pH of the clear liquid was adjusted with sulfuric acid to pH 3.0 to carry out an acidification/crystallization, the solution was filtered to give a solid, the resulting solid was dried over the drying unit to give the DC16 crude product.

To 100 g of the DC16 crude product was added 1500 g of water, and the solution was mixed in the dissolution tank. The mixture was heated to 70° C., followed by adding caustic soda to adjust the pH to 10.2. The mixture was stirred so that hexadecandioic acid was completely dissolved. To the resulted solution was added 9.5 g of microporous powdered sugar charcoal. The mixture was stirred for 1 h and then fed to the separation unit for filtration while hot to give a filtrate. The filtrate was sent to the decolorization tank and further added therein 10 g of microporous powdered sugar charcoal. The mixture was stirred for 1 h and then filtered while hot to give a filtrate. The filtrate was sent to the acidification/crystallization unit, wherein sulfuric acid with a mass percentage concentration of 98% was added to adjust the pH to less than 3. The mixture was cooled to 25° C. to give a solid-liquid mixture, which was then sent to the separation unit for filtration to give the DC16 product.

The relative performances of the products obtained in the above examples and comparative examples were tested and the results are listed in Table 1.

TABLE 1

Performances of the long chain dicarboxylic acid products

| | Total acid content (%) | Purity(%) | Total N content (ppm) | Ash content (ppm) | Fe content (ppm) | Light Transmittance % | Residual solvent (ppm) | Yield % |
|---|---|---|---|---|---|---|---|---|
| Example A | 99.86% | 99.82 | 11 | 9 | 0.6 | 99.6% | Not detected | 91.3 |
| Example B | 99.89% | 99.83 | 11 | 9 | 0.5 | 99.7% | Not detected | 91.2 |
| Example C | 99.92% | 99.86 | 10 | 9 | 0.5 | 99.7% | Not detected | 91.0 |
| Example D | 99.91% | 99.85 | 10 | 8 | 0.5 | 99.8% | Not detected | 91.0 |
| Example 1. DC12 | 99.40% | 99.10% | 26 | 18 | 0.9 | 95% | Not detected | 95.5% |
| Example 2. DC12 | 99.42% | 99.27% | 22 | 16 | 0.8 | 96% | Not detected | 94.5% |
| Example 3. DC16 | 98.88% | 98.80% | 35 | 14 | 0.9 | 92% | Not detected | 95% |
| Example 4-1. DC12 | 99.69% | 99.60% | 20 | 10 | 0.8 | 97.5% | Not detected | 95% |
| Example 4-2. DC12 | 99.55% | 99.22% | 24 | 11 | 0.9 | 97% | Not detected | 95% |
| Example 4-3. DC12 | 99.50% | 99.18% | 24 | 13 | 0.9 | 96.4% | Not detected | 95% |
| Example 5-1. DC12 | 99.73% | 99.65% | 16 | 14 | 0.7 | 98.5% | Not detected | 94% |
| Example 5-2. DC12 | 99.70% | 99.60% | 18 | 15 | 0.8 | 98.4% | Not detected | 94% |
| Example 5-3. DC12 | 99.75% | 99.68% | 15 | 14 | 0.7 | 98.8 | Not detected | 94% |
| Example 6-1. DC12 | 99.80% | 99.70% | 14 | 10 | 0.8 | 99% | Not detected | 91.5% |
| Example 6-2. DC12 | 99.82% | 99.78% | 12 | 10 | 0.6 | 99.5% | Not detected | 91.5% |
| Example 6-3. DC12 | 99.80% | 99.75% | 15 | 11 | 0.7 | 99.1% | Not detected | 92% |
| Example 7. DC12 | 99.65% | 99.59% | 14 | 11 | 0.7 | 99.0% | Not detected | 92.6% |
| Example 8. DC12 | 99.60% | 99.54% | 15 | 11 | 0.8 | 98.6% | Not detected | 93.0% |
| Example 9. DC12 | 99.75% | 99.67% | 13 | 10 | 0.6 | 99.2% | Not detected | 92.5% |
| Comparative Example 1 | 98.50% | 98.01% | 170 | 890 | 3.5 | 90% | Not detected | 95% |
| Comparative Example 2 | 99.30% | 99.05% | 56 | 64 | 1.2 | 94% | 367 | 92% |
| Comparative Example 3 | 97.20% | 96.80% | 340 | 935 | 4.2 | 86% | Not detected | 96% |

Unless otherwise specified, all the terms used in the present disclosure have the meanings conventionally understood by a person skilled in the art.

The embodiments described in the present disclosure are for the purpose of illustration only, not for limiting the scope of the present disclosure. A person skilled in the art may make various substitutions, changes and modifications within the scope of the present disclosure. Therefore, the scope of the present disclosure is not limited to the above embodiments, but is defined by the appended claims.

The invention claimed is:

1. A system for refining long chain dicarboxylic acid, comprising:
   a first membrane filtration unit, for a first membrane filtration of a long chain dicarboxylic acid fermentation broth or a treated liquid therefrom;
   a first decolorization unit, for carrying out a first decolorization treatment to the filtrate obtained after the membrane filtration;
   a first acidification/crystallization unit, for carrying out an acidification/crystallization of a filtrate obtained after the membrane filtration to give a solid-liquid mixture;
   a first separation unit, for a solid-liquid separation of the solid-liquid mixture;
   a drying unit, for drying the solid separated by the separation unit to give a first solid;
   wherein a microfiltration membrane filtration device comprising a microfiltration membrane, an ultrafiltration membrane filtration device comprising an ultrafiltration membrane, and a cooling device are disposed in the first membrane filtration unit; after the microfiltration membrane filtration, the resulted filtrate from the fermentation broth or the treated liquid therefrom is cooled to 20 to 45° C. in the cooling device, and subjected to the ultrafiltration membrane filtration.

2. The refining system according to claim 1, wherein a temperature for the microfiltration membrane filtration is 30 to 100° C.; and/or
   a pore size of the microfiltration membrane is 0.01 to 1 μm; and/or
   the pressure difference on both sides of the membrane during microfiltration filtration is controlled to be 0.05 to 0.5 MPa; and/or
   a temperature for the ultrafiltration membrane filtration is 20 to 100° C.; and/or
   a cut-off molecular weight of the ultrafiltration membrane is 1000 to 200000 Da.

3. The refining system according to claim 1, wherein a temperature for the first decolorization treatment is 50 to 100° C.; and/or
   the acidification/crystallization comprises adjusting the filtrate to pH 2 to 4.5 for crystallization to occur.

4. The refining system according to claim 1, further comprising a vacuum distillation unit, for carrying out separation by distillation on the first solid to obtain a second solid.

5. The refining system according to claim 4, wherein a pressure of the vacuum distillation is ≤100 Pa; and/or the vacuum distillation unit comprises a molecular distillation device for carrying out a molecular distillation or a rectifying column for carrying out a high vacuum distillation.

6. The refining system according to claim 5, wherein the number of plates of the rectifying column is 8 to 24, and/or,
the rectifying column has an overhead pressure of 1 to 100 Pa, and/or,
the rectifying column has an overhead temperature of 160 to 250° C., and/or,
the rectifying column has a bottom temperature of 180 to 270° C., and/or,
the rectifying column has a reflux ratio of (1 to 10):1.

7. The refining system according to claim 5, wherein a pressure in a main evaporator for the molecular distillation is 0.1 to 30 Pa, and/or
the temperature of the evaporation surface of the main evaporator is 130 to 250° C., and/or
the temperature of the condensation surface of the main evaporator is 130 to 160° C.

8. The refining system according to claim 4, comprising a second decolorization unit, which is disposed between the drying unit and the vacuum distillation unit, for carrying out a decolorization treatment to the first solid; or
the second decolorization unit is disposed after the vacuum distillation unit, for carrying out a decolorization treatment to the product obtained after the vacuum distillation.

9. The refining system according to claim 8, wherein the decolorization treatment comprises a melt decolorization; said melt decolorization comprises heating the solid to be decolorized to melt, and passing the same in melt form over a decolorant.

10. The refining system according to claim 9, wherein the temperature for the melt decolorization is 130 to 180° C.; and/or the decolorant is an activated carbon, in the melt decolorization, the amount of the activated carbon is 3 to 50 wt % of the mass of the solid to be decolorized.

11. The refining system according to claim 8, wherein a second acidification/crystallization unit and a second separation unit are disposed between the second decolorization unit and the vacuum distillation unit.

12. The refining system according to claim 1, wherein the pH of the fermentation broth or the treated liquid therefrom is 6 to 12; and/or
before the first membrane filtration, the fermentation broth or the treated liquid therefrom is heated to 60 to 100° C., and/or
before the first filtration unit, a feedstock storage tank and a heating device are disposed, for heating the fermentation broth or the treated liquid therefrom to 60 to 100° C.

13. The refining system according to claim 1, wherein a second membrane filtration unit, a second decolorization unit, a second acidification/crystallization unit, a second separation unit which are sequentially connected, are disposed between the first separation unit and said drying unit; in the second membrane filtration unit, a dissolution tank and a filtration membrane are disposed, said filtration membrane is an ultrafiltration membrane or a microfiltration membrane.

14. The refining system according to claim 13, wherein a third membrane filtration unit is disposed between the second membrane filtration unit and the second decolorization unit; and/or
a third membrane filtration unit is disposed between said second decolorization unit and said acidification/crystallization unit.

15. The refining system according to claim 14, wherein a filtration membrane is disposed in the third membrane filtration unit, said membrane filtration unit is an ultrafiltration membrane.

16. The refining system according to claim 1, wherein a decolorization tank, a plate-and-frame filter and a heating device are disposed in the first decolorization unit.

17. The refining system according to claim 12, wherein the pH of the fermentation broth or the treated liquid therefrom is 8 to 11.

18. A system for refining long chain dicarboxylic acid, comprising:
a first membrane filtration unit, for a first membrane filtration of a long chain dicarboxylic acid fermentation broth or a treated liquid therefrom;
a first decolorization unit, for carrying out a first decolorization treatment to the filtrate obtained after the membrane filtration;
a first acidification/crystallization unit, for carrying out an acidification/crystallization of a filtrate obtained after the membrane filtration to give a solid-liquid mixture;
a first separation unit, for a solid-liquid separation of the solid-liquid mixture;
a drying unit, for drying the solid separated by the separation unit to give a first solid;
a vacuum distillation unit, for carrying out separation by distillation on the first solid to obtain a second solid;
wherein a pressure of the vacuum distillation is ≤100 Pa; and the vacuum distillation unit comprises a rectifying column for carrying out a high vacuum distillation, and
wherein the number of plates of the rectifying column is 8 to 24, and/or,
the rectifying column has an overhead pressure of 1 to 100 Pa, and/or,
the rectifying column has an overhead temperature of 160 to 250° C., and/or,
the rectifying column has a bottom temperature of 180 to 270° C., and/or,
the rectifying column has a reflux ratio of (1 to 10):1.

19. The refining system according to claim 18, wherein the first membrane filtration unit comprises a microfiltration membrane and/or an ultrafiltration membrane.

20. The refining system according to claim 19, wherein a temperature for the microfiltration membrane filtration is 30 to 100° C.; and/or
a pore size of the microfiltration membrane is 0.01 to 1 µm; and/or
the pressure difference on both sides of the membrane during microfiltration filtration is controlled to be 0.05 to 0.5 MPa; and/or
a temperature for the ultrafiltration membrane filtration is 20 to 100° C.; and/or
a cut-off molecular weight of the ultrafiltration membrane is 1000 to 200000 Da.

21. The refining system according to claim 18, wherein a temperature for the first decolorization treatment is 50 to 100° C.; and/or
the acidification/crystallization comprises adjusting the filtrate to pH 2 to 4.5 for crystallization to occur.

22. The refining system according to claim 18, comprising a second decolorization unit, which is disposed between the drying unit and the vacuum distillation unit, for carrying out a decolorization treatment to the first solid; or
- the second decolorization unit is disposed after the vacuum distillation unit, for carrying out a decolorization treatment to the product obtained after the vacuum distillation.

23. The refining system according to claim 22, wherein the decolorization treatment comprises a melt decolorization; said melt decolorization comprises heating the solid to be decolorized to melt, and passing the same in melt form over a decolorant.

24. The refining system according to claim 23, wherein the temperature for the melt decolorization is 130 to 180° C.; and/or
- the decolorant is an activated carbon, in the melt decolorization, the amount of the activated carbon is 3 to 50 wt % of the mass of the solid to be decolorized.

25. The refining system according to claim 22, wherein a second acidification/crystallization unit and a second separation unit are disposed between the second decolorization unit and the vacuum distillation unit.

26. The refining system according to claim 18, wherein the pH of the fermentation broth or the treated liquid therefrom is 6 to 12; and/or
- before the first membrane filtration, the fermentation broth or the treated liquid therefrom is heated to 60 to 100° C., and/or
- before the first filtration unit, a feedstock storage tank and a heating device are disposed, for heating the fermentation broth or the treated liquid therefrom to 60 to 100° C.

27. The refining system according to claim 26, wherein the pH of the fermentation broth or the treated liquid therefrom is 8 to 11.

28. The refining system according to claim 18, wherein a second membrane filtration unit, a second decolorization unit, a second acidification/crystallization unit, a second separation unit which are sequentially connected, are disposed between the first separation unit and said drying unit; in the second membrane filtration unit, a dissolution tank and a filtration membrane are disposed, said filtration membrane is an ultrafiltration membrane or a microfiltration membrane.

29. The refining system according to claim 28, wherein a third membrane filtration unit is disposed between the second membrane filtration unit and the second decolorization unit; and/or a third membrane filtration unit is disposed between said second decolorization unit and said acidification/crystallization unit.

30. The refining system according to claim 29, wherein a filtration membrane is disposed in the third membrane filtration unit, said membrane filtration unit is an ultrafiltration membrane.

31. The refining system according to claim 18, wherein a decolorization tank, a plate-and-frame filter and a heating device are disposed in the first decolorization unit.

* * * * *